(12) United States Patent
Zanutto et al.

(10) Patent No.: US 7,901,698 B2
(45) Date of Patent: Mar. 8, 2011

(54) PHARMACEUTICAL COMPOSITIONS COMPRISING SILICONES AND TWO SOLUBILIZED ACTIVE PRINCIPLES

(75) Inventors: Leslie Zanutto, Paulhaguet (FR); Sandrine Orsoni, Mandelieu (FR); Claire Mallard, Mougins le Haut (FR); Emilie Tonglet, Golfe de Juan (FR)

(73) Assignee: Galderma S.A., Cham (CH)

( * ) Notice: Subject to any disclaimer, the term of this patent is extended or adjusted under 35 U.S.C. 154(b) by 802 days.

(21) Appl. No.: 10/951,887

(22) Filed: Sep. 29, 2004

(65) Prior Publication Data
US 2005/0282788 A1 Dec. 22, 2005

(30) Foreign Application Priority Data
Jun. 17, 2004 (FR) .................................. 04 06610

(51) Int. Cl.
*A61K 8/02* (2006.01)
(52) U.S. Cl. ........................................ 424/401
(58) Field of Classification Search .................. 424/401
See application file for complete search history.

(56) References Cited

U.S. PATENT DOCUMENTS

| | | | |
|---|---|---|---|
| 4,308,264 A | 12/1981 | Conway et al. | |
| 4,738,956 A | 4/1988 | Scott et al. | |
| 5,254,334 A * | 10/1993 | Ramirez et al. | 424/70.24 |
| 6,136,332 A | 10/2000 | Grollier et al. | |
| 6,759,396 B1 | 7/2004 | Michel et al. | |
| 2002/0018791 A1* | 2/2002 | Vatter et al. | 424/401 |
| 2003/0091522 A1* | 5/2003 | Collins et al. | 424/70.7 |
| 2003/0170194 A1 | 9/2003 | Piotrowiak et al. | |
| 2007/0190124 A1* | 8/2007 | Zhang et al. | 424/448 |

FOREIGN PATENT DOCUMENTS

| | | |
|---|---|---|
| CA | 2 148 112 C | 1/2001 |
| EP | 0679392 A1 | 11/1995 |
| EP | 0755675 A1 | 1/1997 |
| EP | 0 998 943 A1 | 5/2000 |
| FR | 2738745 A1 | 3/1997 |
| WO | WO 00/64450 | 11/2000 |
| WO | WO 01/87344 A1 | 11/2001 |

OTHER PUBLICATIONS

Fenton et al. Journal of Clinical Dermatology, 2004, p. 463-478.*
Alberg et al., "Investigations on the long-term stability of corticosteroids in modified water containing hydrophilic ointment," *Pharm Pharmacol Lett*, 8 (1988) 2:53-56, Medpharm Scientific Publishers.
International Preliminary Report on Patentability for corresponding PCT/EP2005/007974 issued Dec. 20, 2006 in English.
International Search Report for corresponding PCT/EP2005/007974 issued Nov. 3, 2005 in English.

* cited by examiner

*Primary Examiner* — Sreeni Padmanabhan
*Assistant Examiner* — Samira Jean-Louis
(74) *Attorney, Agent, or Firm* — Buchanan Ingersoll & Rooney PC

(57) ABSTRACT

Topically applicable, anhydrous and physically/chemically stable pharmaceutical compositions useful for the treatment of disorders of the skin, notably psoriasis, contain a silicone agent; a therapeutically effect amount of a compound A, which is vitamin D or derivative thereof, solubilized in a solvent therefor; and a therapeutically effective amount of a compound B, which is the corticosteroids, also solubilized in a solvent therefor.

2 Claims, No Drawings

PHARMACEUTICAL COMPOSITIONS COMPRISING SILICONES AND TWO SOLUBILIZED ACTIVE PRINCIPLES

CROSS-REFERENCE TO PRIORITY APPLICATION

This application claims priority under 35 U.S.C. §119 of FR 04/06610, filed Jun. 17, 2004, hereby expressly incorporated by reference and assigned to the assignee hereof.

BACKGROUND OF THE INVENTION

1. Technical Field of the Invention

The present invention relates to the formulation of active principles into pharmaceutical compositions useful for topical pharmaceutical applications.

The present invention relates more particularly to stable anhydrous pharmaceutical compositions comprising a silicone agent and, as bioaffecting active principles, vitamin D or a vitamin D derivative and a corticosteroid, to the process for preparing same and to administration thereof for the topical treatment of psoriasis and other skin disorders.

2. Description of Background and/or Related and/or Prior Art

Vitamin D and its derivatives are generally used in dermatology in the treatment of psoriasis since they limit the excessive production of cutaneous cells on the surfaces affected and possess proven advantages for the treatment of this ailment, which is characterized in particular by the presence of thick, squamous and dry lesions.

It is known that a certain number of active principles which exhibit advantageous therapeutic activity are sensitive to oxidation and in particular undergo chemical degradation leading to a substantial loss in their activity in the presence of water.

The combination in a single pharmaceutical composition of vitamin D or a vitamin D derivative with a corticosteroid is not without its problems. This is because vitamin D or some vitamin D derivatives are unstable in an acidic environment (they have maximum stability at pH values of approximately 8) and certain corticosteroids are unstable in a basic environment (they exhibit maximum stability at a pH of approximately 4 to 6).

Consequently, it is appropriate to formulate these active principles in anhydrous compositions.

The anhydrous compositions presently available on the market which allow the formulation of water-sensitive active principles while ensuring their effective chemical stability are generally ointment compositions. These ointment compositions are composed principally of petroleum jelly, mineral oil and/or vegetable oil. Certain of the compositions comprising petroleum jelly, however, are considered after application to be sticky and greasy, and in addition are shiny. The greasy residue left on the skin prevents the patient afflicted by psoriasis from putting on his or her clothes again after treatment without the risk of leaving greasy marks thereon, which does not necessarily encourage the patient to follow his or her treatment. Non-compliance with the prescribed treatment is one of the main causes of failure; the article "*Patients with psoriasis and their compliance with medication*, Richards et al., *J. Am. Acad. Dermatol.*, October 1999, pp. 581-583" indicates that almost 40% of patients with a chronic disease such as psoriasis do not follow their treatment. The characteristics of the vehicle used in the pharmaceutical compositions are directly linked to the adherence by the patient to his or her treatment.

The ointment compositions presently on the market do not always lend themselves to the formulation of the active principle in a solubilized form.

EP-0,255,369 and U.S. Pat. No. 6,103,250 describe formulations based for the most part on silicone derivatives, in which the water-sensitive active substances are formulated in a dispersed form. The dispersed form, however, is generally detrimental to optimum skin penetration and/or release of these active substances.

SUMMARY OF THE INVENTION

Novel anhydrous pharmaceutical compositions suited for topical application have now been developed that ameliorate or avoid the abovementioned drawbacks and disadvantages of the prior art.

The present invention thus features anhydrous pharmaceutical compositions suited for topical application wherein the active principles/agents are in a solubilized state and exhibit prolonged stability.

The present invention also features anhydrous pharmaceutical compositions suited for the treatment of psoriasis, which comprise a silicone agent and, as active principles, a compound A selected from among vitamin D or a vitamin D derivative and a compound B selected from among corticosteroids, the said compounds A and B each being in a solubilized form or state in said compositions.

The compositions of the invention are more particularly intended for topical application.

DETAILED DESCRIPTION OF BEST MODE AND SPECIFIC/PREFERRED EMBODIMENTS OF THE INVENTION

The active principles are in the solubilized state, thereby imparting to the compositions of the invention effective properties of release/skin penetration of each of the said active principles, in conjunction with more advantageous kinetics. The term "effective release/penetration capacity" refers to the effective distribution of the compositions of the invention and hence of the active principles it comprises across the stratum corneum of the skin and also across the subcutaneous layers such as the epidermis and the dermis.

In particular, the pharmaceutical compositions according to the present invention are such that the difference in optimum pH stability of the compound A and the optimum pH stability of the compound B is at least 1.

The term "anhydrous composition" refers for the purposes of the present invention to a composition which is substantially free of water, which is to say that it has a water content of less than or equal to 5% by weight relative to the total weight of the composition, in particular less than or equal to 3%, and especially zero.

The active principles forming part of the compositions of the invention, namely vitamin D or a vitamin D derivative and a corticosteroid, possess a therapeutic activity against dermatological ailments or skin complaints, conditions or afflictions such as, for example, psoriasis. By vitamin D is meant the various forms of vitamin D such as, for example, vitamin $D_1$, $D_2$, $D_3$ or vitamin $D_4$.

By vitamin D derivatives are meant compounds which exhibit biological properties analogous to those of vitamin D, especially properties of transactivation of vitamin D response elements (VDREs), such as an agonist or antagonist activity with regard to receptors of vitamin D or its derivatives. These compounds are not generally natural metabolites of vitamin D. The compounds in question are, in particular, synthetic compounds comprising the vitamin D skeleton with modifications on the side chains and/or likewise comprising modifications within the skeleton itself. Vitamin D derivatives useful according to the invention thus comprise structural analogues: biaromatics, for example.

By way of illustration of vitamin D derivatives, mention may be made in particular of calcipotriol, calcitriol or 1,25-dihydroxyvitamin $D_3$, doxercalciferol, secalcitol, maxacalcitol, seocalcitol, tacalcitol, paricalcitol, falecalcitriol, $1\alpha$,24S-dihydroxyvitamin D2, 1(S),3(R)-dihydroxy-20(R)-[((3-(2-hydroxy-2-propyl)phenyl)methoxy)methyl]-9,10-secopregna-5(Z),7(E),10(19)-triene and mixtures thereof.

According to one preferred embodiment of the invention, the vitamin D derivative is calcitriol.

As vitamin D derivatives which can be used according to the invention, mention may also be made of the derivatives described in WO 02/34235, WO 00/64450, E-1,124,779, EP-1,235,824, EP-1,235,777, WO 02/94754, WO 03/050067 and WO 00/26167. The compounds described in WO 00/26167 concern structural analogues of vitamin D which exhibit selective activity on proliferation and on cell differentiation without exhibiting any hypercalcemic character.

Advantageously, the amount of vitamin D or vitamin D derivative in solubilized form in the composition of the invention is from 0.00001 to 5% by weight relative to the total weight of the composition, preferably from 0.0001 to 3% by weight and more particularly from 0.0003 to 1% by weight.

By corticosteroid is meant for the purposes of the present invention a topical steroid from group I, II, III or IV (strong and weak).

According to one advantageous embodiment of the invention, the corticosteroid is selected from the group consisting of betamethasone, clobetasol, clobetasone, desoxymethasone, diflucortolone, diflorasone, fluocinonide, flumethasone, fluocinolone, fluticasone, fluprednidene, halcinonide, hydrocortisone, mometasone, triamcinolone and their pharmaceutically acceptable esters and acetonides and mixtures thereof.

As examples of esters or acetonides, mention may be made of those selected from the group consisting of the 17-valerate, 17-propionate, 17,21-dipropionate, acetonide, acetonide-21-N-benzoyl-2-methyl-β-alaninate, acetonide-21-(3,3-dimethylbutyrate) and 17-butyrate.

According to one preferred embodiment of the invention, the corticosteroid is clobetasol 17-propionate.

Advantageously, the amount of corticosteroid in solubilized form in the composition of the invention is from 0.0001 to 1% by weight relative to the total weight of the composition, preferably from 0.00005 to 3% by weight, and more particularly from 0.001 to 0.1% by weight.

According to one advantageous embodiment of the invention, the active principles are solubilized in the same solvent or in two or more solvents.

The solvent of the present invention is selected from pharmaceutically acceptable compounds, which is to say compounds whose use is compatible in particular with application to the skin, the mucosae and/or the keratin fibers. The solvent is generally fluid, and in particular liquid, at ambient temperature and atmospheric pressure.

As solvents according to the invention, mention may be made in particular of the following:
  linear or branched aliphatic alcohols having 1 to 6 carbon atoms such as ethanol, isopropanol, butanol and mixtures thereof; preferably the solvent is ethanol;
  oils such as caprylic and capric triglycerides (Miglyol 812), cetearyl isononanoate (Cetiol SN), vegetable oils such as sweet almond oil, sesame oil, wheatgerm oil, olive oil and mixtures thereof; and mixtures thereof.

As a suitable solvent in the compositions of the invention, mention may also be made of:
  compounds of general formula $R^3(OCH_2C(R^1)H)_xOR^2$, in which x is an integer ranging from 2 to 60, $R^1$ in each of the x units is independently H or $CH_3$, $R^2$ is a linear or branched $C_{1-20}$ alkyl or a benzoyl radical and $R^3$ is H or a phenylcarbonyloxy radical;
  $C_{4-8}$ dicarboxylic acid di(linear or branched $C_{4-10}$ alkyl) esters; and
  linear or branched $C_{12-18}$ alkyl benzoates.

It will be appreciated that the selection of the solvent depends in particular on the active principle to be solubilized. According to one preferred embodiment of the invention, when the active principles are calcitriol and clobetasol 17-propionate, the solvent is more particularly absolute ethanol.

The solvent is generally present in the compositions of the invention in an amount which is on the one hand sufficient to provide the required solubility of the active principles to be formulated and which on the other hand is compatible with the need to preserve prolonged chemical stability of these active principles. In other words, the solvent must be chemically inert towards the active principles.

Advantageously, the amount of solvent in a composition of the invention is from 1 to 50% by weight relative to the total weight of the composition, preferably from 2 to 40% by weight and more particularly from 5 to 20% by weight.

The solvent likewise confers a beneficial effect on the skin penetration rate of the active principles.

Moreover, the solvent may also be useful for promoting the compatibility of the silicone agent with one or more other components present in the composition.

According to one advantageous embodiment of the invention, the silicone agent comprises at least one organopolysiloxane elastomer.

By organopolysiloxane elastomer is meant any chemically crosslinked siloxane polymer which exhibits viscoelastic properties.

Organopolysiloxane elastomers which can be used in the compositions of the invention are described in particular in U.S. Pat. Nos. 4,980,167 and 4,742,142. The compounds in question may in particular be compounds resulting from addition reactions, i.e., products of hydrosilylation or products of polymerization obtained from the addition of an organopolysiloxane having unsaturated groups such as vinyl or allyl groups, linked in particular to at least one terminal Si atom, and another silicone compound capable of participating in the addition reaction, such as an organohydropolysiloxane.

According to one particular embodiment of the invention, the organopolysiloxane elastomer is formulated in a vehicle comprising at least one volatile silicone oil.

By a volatile silicone oil is meant any silicone oil capable of evaporating on contact with the skin, the mucosae or the keratin fibers in less than one hour at ambient temperature and atmospheric pressure.

As examples of volatile silicone oils, mention may be made, for example, of linear or cyclic polyorganosiloxane oils having in particular 2 to 10 silicon atoms and optionally containing alkyl or alkoxy groups having 1 to 22 carbon atoms. These silicone oils exhibit in particular a viscosity of less than or equal to 6 centistokes ($6 \times 10^{-6}$ $m^2/s$).

The volatile silicone oils include in particular the low molecular weight cyclomethicones and dimethicones or mixtures thereof. In particular the volatile silicone oils are selected from cyclic methyl organopolysiloxanes having ring sizes ranging from 4 to 12, such as octamethylcyclotetrasiloxane and decamethylcyclopentasiloxane. As a volatile silicone oil which can be used in the invention, mention may also be made of dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

Among the silicone agents which may be used in the compositions of the invention, mention may be made in particular of ST Elastomer 10® from Dow Corning, which is a silicone elastomer formulated in a deca-methylcyclopentasiloxane oil, in the form of a thick, translucent gel.

The above-defined silicone agent may fulfill in particular the function of a thickener in the compositions according to the invention. It may further be involved in stabilizing the said compositions.

Likewise suitable for the compositions according to the invention are silicone agents such as those prepared by crosslinking reaction between polysiloxanes (A) containing ≡Si—H groups, an alpha, omega-diene (B) in the presence of a catalyst and a low molecular weight cyclic or linear polysiloxane (C).

The polysiloxane (A) containing the ≡Si—H unit may be represented by compounds of formula $R^{14}_3SiO(R^{15}_2SiO)_a(R^{16}HSiO)_bSiR^{14}_3$, denoted here as type $A^1$, and the compounds of formula $HR^{14}_2SiO(R^{15}_2SiO)_cSiR^{14}_2H$ or of formula $HR^{14}_2SiO(R^5_2SiO)_a(R^{16}HSiO)_bSiR^{14}_2H$, denoted here as type $A^2$. In these formulae $R^{14}$, $R^{15}$ and $R^{16}$ are alkyl groups having one to six carbon atoms, a is an integer varying from 0 to 250, b is an integer varying from 1 to 250 and c is an integer varying from 0 to 250. The molar ratio of the compounds, $A^2:A^1$, is from 0 to 20, in particular from 0 to 5.

The alpha, omega-diene (B) is a compound of formula $CH_2=CH(CH_2)_dCH=CH_2$ in which d is an integer varying from 1 to 20. Representative examples of appropriate alpha, omega-dienes are 1,4-pentadiene, 1,5-hexadiene, 1,6-heptadiene, 1,7-octadiene, 1,8-nonadiene, 1,9-decadiene, 1,11-dodecadiene, 1,13-tetradecadiene, and 1,19-eicosadiene.

The expression "low molecular weight polysiloxane (C)" encompasses:

linear, cyclic or branched volatile methylsiloxanes of low molecular weight;

linear or cyclic, volatile or non-volatile alkyl- and arylsiloxanes of low molecular weight; and linear or cyclic functional siloxanes of low molecular weight.

Advantageously, the oil (C) is selected from linear or cyclic volatile methylsiloxanes of low molecular weight.

As linear volatile methylsiloxanes, mention may be made of hexamethyldisiloxane, octamethyltrisiloxane, decamethyltetrasiloxane, dodecamethylpentasiloxane, tetradecamethylhexasiloxane and hexadecamethylheptasiloxane.

As cyclic volatile methylsiloxanes, mention may be made of hexamethylcyclotrisiloxane, octamethylcyclotetrasiloxane, decamethylcyclopentasiloxane and dodecamethylcyclohexasiloxane.

As branched volatile methylsiloxanes, mention may be made in particular of heptamethyl-3-[(trimethylsilyl)oxy]trisiloxane, hexamethyl-3,3-bis[(trimethylsilyl)oxy]trisiloxane, and pentamethyl[(trimethylsilyl)oxy]cyclotrisiloxane.

Likewise suitable in the present invention are non-volatile, low molecular weight polysiloxanes of the general formula:

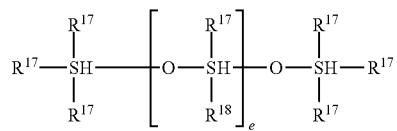

in which:

e is such that the polymers conforming to this formula exhibit a viscosity in the range of approximately 100 to 1000 centistokes (mm²/sec), and are selected in particular from the range from 80 to 375, $R^{17}$ and $R^{18}$ are alkyl radicals having 1 to 20 carbon atoms or an aryl group such as a phenyl group.

Among these polysiloxanes, mention may be made in particular of polydimethylsiloxane, polydiethylsiloxane, polymethylethylsiloxane, polymethylphenylsiloxane and polydiphenylsiloxane.

Functionalized polysiloxanes of low molecular weight may be represented by fluid siloxanes which carry acrylamide, acrylate, amide, amino, carbinol, carboxyl, chloroalkyl, epoxy, glycol, ketal, mercapto, methyl ester, perfluoro and silanol functions.

Such elastomers are described in particular in U.S. Pat. No. 5,654,362.

Likewise suitable as silicone agents in accordance with the invention are silicone polymers having an average molecular weight of at least 10,000 (for example ranging from 10,000 to 10,000,000). Examples of silicone polymers include crosslinked siloxane copolymers, for example copolymers of dimethicone or dimethicone derivatives, such as the stearylmethyl-dimethylsiloxane copolymer (Gransil SR-CYC® from the company Grant Industries), Polysilicone-11® (i.e., a crosslinked silicone elastomer formed by reacting vinyl-terminated silicone and methylhydrodimethylsiloxane in the presence of cyclomethicone), crosslinked cetearyldimethicone/vinyidimethicone copolymers (i.e., a cetearyldimethicone copolymer crosslinked with a vinyldimethylpolysiloxane), a crosslinked dimethicone/phenylvinyidimethicone polymer (i.e., a dimethylpolysiloxane copolymer crosslinked with phenylvinyldimethylsiloxane), and a crosslinked dimethicone/vinyldimethicone copolymer (i.e., a dimethylpolysiloxane copolymer crosslinked with vinyldimethylsiloxane).

Silicone gels of this kind may be obtained commercially in particular from Grant Industries. Examples of such gels include the mixture of cyclomethicone and polysilicone-11 sold for example under the name Gransil GCM5®, the mixture of cyclotetrasiloxane and polysilicone-11 sold for example under the name Gransil PS-4®, the mixture of cyclopentasiloxane and polysilicone-11 sold for example under the name Gransil PS-5®, the mixture of cyclopentasiloxane, dimethicone and polysilicone-11 sold for example under the name Gransil DMCM-5®, the mixture of cyclotetrasiloxane, dimethicone and polysilicone-11 sold for example under the name Gransil DMCM-4®, the mixture of polysilicone-11 and isododecane sold for example under the name Gransil IDS®, and the mixture of cyclomethicone, polysilicone-11 and phytosphingosine sold for example under the name Gransil SPH®. Examples of gels available from the company General Electric include in particular a crosslinked polymer called cyclopentasiloxane and dimethicone/vinyldimethicone crosspolymer SFE839®.

Other silicone gels may also be obtained commercially in particular from Shin-Etsu under the following references: KSG-15, KSG-16 and KSG-17.

According to one particular embodiment, the composition according to the invention is devoid of organopolysiloxane elastomer carrying alkyl groups.

Advantageously, the amount of silicone agent in a composition of the invention is from 20 to 95% by weight relative to the total weight of the composition, preferably from 30 to 80% by weight.

The amount of organopolysiloxane elastomer in a composition of the invention may vary substantially, in particular depending on the viscosity of the desired composition.

Advantageously, the amount of organopolysiloxane elastomer in a composition of the invention is from 20 to 90% by weight relative to the total weight of the composition, preferably from 30 to 80% by weight.

The compositions according to the invention may further comprise various other ingredients. The selection of these supplementary ingredients, like that of their respective amounts, is made so as not to adversely affect the expected properties of the composition. In other words, these compounds must not adversely affect the chemical stability of the active principles or their solubility.

According to one advantageous embodiment of the invention, the compositions further comprise an antioxidant selected from the group consisting of butylated hydroxytoluene (BHT), butylated hydroxyanisole (BHA), DL-alpha-tocopherol, superoxide dismutase, ubiquinol or certain chelating agents.

According to another advantageous embodiment, the compositions further comprise an oily additive selected from the group consisting of isopropyl palmitate, dicaprylyl ether, dimethicone or mixtures thereof.

In the compositions of the invention, the addition of an oily additive makes it possible to avoid fluffing and to have a light, more substantive residue from the standpoint of the treatment of psoriasis.

The compositions of the invention may further comprise one or more pharmaceutical excipients suitable for topical application.

By way of examples of pharmaceutical excipients suitable for topical application, mention may be made of:
  wetting agents;
  flavor enhancers;
  stabilizers;
  moisture regulators;
  pH regulators;
  osmotic pressure modifiers;
  emulsifiers;
  UV-A and UV-B filters;
  penetration promoters;
  and synthetic polymers.

As will be appreciated, one skilled in the art will ensure that any compound or compounds to be added to these compositions will be selected such that the advantageous properties intrinsically associated with the present invention are not, or not substantially, adversely affected by the intended addition.

According to one advantageous embodiment of the invention, the composition is in the form of an ointment, gel, cream or unguent.

Preferably, the compositions of the invention are in the form of an ointment. For the purposes of the present invention and in accordance with the U.S. Pharmacopeia (USP) an ointment is a semisolid preparation intended for external application to the skin or mucosae. Ointments or unguents are used topically for numerous applications, for example as barrier creams, antiseptic creams, emollient creams, etc. Ointments are used for their emollient effect; they are simple to apply and readily penetrate the skin.

Advantageously, the compositions according to the invention prove, following application, to be exempt from effects of stickiness, greasiness and shine and instead to provide a soft feel. This new type of ointment enhances absorption through the skin, leaves a non-greasy powdery residue and provides ease of application, allowing improvement in the adherence by the patient to his or her treatment. Moreover, one advantageous aspect of this composition is the absence of preservative.

Additionally, the inventive compositions show themselves to be particularly effective for preserving satisfactory chemical stability of the active principles which are sensitive to oxidation, to water and to aqueous environments in general. The term "satisfactory chemical stability" applies to a composition which, over a period of at least three months, respectively at ambient temperature and at 40° C.:
  does not present any substantial modification of its macroscopic appearance,
  has an active principles content of at least 70%, in particular at least 80% and more particularly at least 95% of the initial weight content.

The present invention likewise features the use of a silicone agent for preparing an anhydrous pharmaceutical composition suited for a regime or regimen for the treatment of psoriasis, said composition comprising as active principles vitamin D or a vitamin D derivative and a corticosteroid, and said active principles each being in a solubilized form.

In the abovementioned use, the pharmaceutical compositions are as defined above.

According to one advantageous embodiment of the invention, the composition is prepared cold, in other words at ambient temperature between 20° C. and 25° C. The composition is prepared by mixing at least two distinct phases: a phase comprising at least the silicone agent and a phase comprising at least the active principles and the solvent or solvents of the said active principles.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Solubility and Stability Tests on the Active Principles

The stability of calcitriol was tested in various solvents, including ethanol 100 and a 75%/25% ethanol 100/cyclomethicone mixture.

a) Stability of Calcitriol in Ethanol:

A 30 ppm solution of calcitriol in absolute ethanol to 100% is prepared in the presence of 0.02% of butylated hydroxytoluene (BHT).

The results of an HPLC assay technique against a reference are indicated in table 1 below.

At the starting time (T0) the calcitriol concentration is taken to be 100%.

TABLE 1

| Stability conditions | T1 week | T2 weeks | T3 weeks | T4 weeks |
|---|---|---|---|---|
| −18° C. | 100.9% | 100.5% | 99.5% | 99.5% |
| +4° C. | 97.7% | 98.6% | 98.1% | 97.7% |
| +30° C. | / | 93.4% | / | 93.0% | b) Stability of Calcitriol in the (Ethanol/Cyclopentasiloxane) Mixture

A 30 ppm solution of calcitriol in absolute ethanol to 100% is prepared in the presence of 0.02% of BHT.

The results of an HPLC assay technique against a reference are indicated in table 2 below.

At the starting time (T0) the calcitriol concentration is taken to be 100%.

TABLE 2

| Stability conditions | T2 weeks | T3 weeks | T4 weeks |
|---|---|---|---|
| −18° C. | 100.4% | 101.3% | 99.2% |
| +4° C. | 99.2% | 99.6% | 97.5% |
| +30° C. | 93.8% | / | 93.3% |

Example 2

Preparation of a Composition of the Invention

The process described below is a general process for preparing a silicone ointment comprising a vitamin D derivative and a corticosteroid. The process is carried out at ambient temperature, between 20° C. and 25° C.

a) First Step: Preparation of the Phase Comprising the Silicone Agent (Phase A):

The constituents of phase A are weighed out into a beaker: Elastomer ST 10®, silicone oil and oily additive.

These constituents are homogenized until a homogeneous gel is obtained.

b) Second Step: Preparation of the Phase Comprising the 5 Active Principles (Phase B):

A stock solution is prepared which comprises a vitamin D derivative in an appropriate solvent and an antioxidant. The solution is stirred until the active dissolves.

The corticosteroid is weighed out and placed in its solvent. The solution is stirred until the active dissolves.

The two active phases are incorporated into phase A with stirring. The mixture is homogenized.

When the solvent is the same for both active principles, the corticosteroid is added to the stock solution of the vitamin D derivative.

Example 3

Examples of Pharmaceutical Compositions of the Invention

TABLE 3

Composition 1

| (1) Ingredients | Amounts in % weight per weight |
|---|---|
| ISOPROPYL PALMITATE (oily additive) | 1 |
| CYCLOPENTASILOXANE (solvent) | 16 |
| CYCLOMETHICONE 5/DIMETHICONE CROSSPOLYMER (silicone agent) | 74.9347 |
| BUTYLHYDROXYTOLUENE (antioxidant) | 0.04 |
| CALCITRIOL (active) | 0.0003 |

TABLE 3-continued

Composition 1

| (1) Ingredients | Amounts in % weight per weight |
|---|---|
| CLOBETASOL PROPIONATE (active) | 0.025 |
| ABSOLUTE ETHANOL (solvent) | 8 |

The physical stability of the compositions is measured by macroscopic and microscopic observation of the composition at ambient temperature, at 4° C. and at 40° C. after 15 days, 1 month, 2 months and 3 months.

CONCLUSION

At ambient temperature the macroscopic observation makes it possible to ensure the physical integrity of the compositions and the microscopic observation makes it possible to verify that there is no recrystallization of the solubilized active principles.

At 4° C. the microscopic observation verifies the non-recrystallization of the solubilized active principles.

At 40° C. the macroscopic observation verifies the integrity of the final composition.

Characterization of the final composition is completed with a measurement of the flow point. A Haake rheometer of type VT550 is used with a SVDIN measuring spindle. The rheograms are performed at 25° C. and at a shear rate of 4 s$^{-1}$ ($\gamma$), measuring the shearing stress. By flow point ($\tau$0 expressed in pascals) is meant the force required (minimum shearing stress) to overcome the van der Waals cohesion forces and bring about the flow. The flow point is taken to be the value found at a shear rate of 4 s$^{-1}$.

These measurements are carried out at T0 and after 1, 2 and 3 months.

These measurement techniques show that the composition of the invention is stable at least for 1 month at 4° C. and 40° C.

| SPECIFICATIONS AT T0 | | | | |
|---|---|---|---|---|
| tau 0 | | 14 | Macroscopic appearance | Fluid transparent ointment |
| Centrifugation | 3000 rpm | RAS | Microscopic appearance | No crystals of actives |
| | 10000 rpm | exudate | | |

| | | T15 d | T1 month |
|---|---|---|---|
| Macroscopy | | COMPLIES | COMPLIES |
| Microscopy | | COMPLIES | COMPLIES |
| tau 0 | | 15 | 18 |
| Centrifugation | 3000 | COMPLIES | COMPLIES |
| | 10000 | COMPLIES | COMPLIES |
| Macroscopy | | COMPLIES | COMPLIES |
| Microscopy | | COMPLIES | COMPLIES |
| Macroscopy | | COMPLIES | COMPLIES |
| Microscopy | | COMPLIES | COMPLIES |
| tau 0 | | 14 | 14 |

TABLE 4

| (2) Ingredients | Amounts in % wt per wt |
|---|---|
| DICAPRYLYL ETHER (oily additive) | 15 |
| BUTYLATED HYDROXYTOLUENE (antioxidant) | 0.04 |
| CALCITRIOL (active) | 0.0003 |
| CYCLOPENTASILOXANE (solvent) | 8 |
| CYCLOMETHICONE 5/DIMETHICONE CROSSPOLYMER (silicone agent) | 75.935 |
| CLOBETASOL PROPIONATE (active) | 0.025 |
| ABSOLUTE ETHANOL (solvent) | 1 |

The physical stability of the compositions is measured as described above. The conclusions are identical with what was described before.

TABLE 5

| (3) Ingredients | Amounts in % wt per wt |
|---|---|
| DIMETHICONE 200-350cSt | 1 |
| CYCLOPENTASILOXANE | 12 |
| CYCLOMETHICONE 5/DIMETHICONE CROSSPOLYMER | qs 100 |
| BUTYLATED HYDROXYTOLUENE | 0.04 |
| CALCITRIOL | 0.0003 |
| CLOBETASOL PROPIONATE | 0.025 |
| ABSOLUTE ETHANOL | 8 |

The physical stability of the compositions is measured as described above. The conclusions are identical with what was described before.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical composition for use in the treatment of psoriasis, consisting essentially of:
    (a) cyclomethicone 5/dimethicone crosspolymer, in an amount of from 74.9347 to about 78.9347% by weight relative to the total weight of the composition;
    (b) calcitriol, in an amount of 0.0003% by weight relative to the total weight of the composition;
    (c) clobetasol 17-propionate, in an amount of 0.025% by weight relative to the total weight of the composition;
    (d) at least two solvents in which (b) and (c) are solubilized which are at least absolute ethanol and cyclopentasiloxane;
    (e) an oily additive selected from the group consisting of isopropyl palmitate, dicapryl ether and dimethicone; and
    (f) butylated hydroxytoluene;
    said composition having a zero water content and being physically stable for at least one month at 4° C. and 40° C.

2. A regime or regimen for the treatment of psoriasis, comprising topically applying onto the affected area of the skin of an individual afflicted with psoriasis, an anti-psoriasis effective amount of a composition as defined in claim 1.

* * * * *